United States Patent

[11] 4,055,166

Simpson et al.

[45] Oct. 25, 1977

[54] APPARATUS FOR MAKING SURFACE TEMPERATURE MEASUREMENTS ON THE HUMAN BODY

[76] Inventors: Hugh Walter Simpson, 2 Kirklee Terrace, Glasgow; Douglas Green, 1 Kingsmill Drive, Kennoway, both of Scotland

[21] Appl. No.: 594,555

[22] Filed: July 9, 1975

[51] Int. Cl.² .................. A61B 5/00; G01K 1/02
[52] U.S. Cl. .................... 128/2 H; 73/342; 73/343.5
[58] Field of Search .................. 73/340–342, 73/343.5; 128/2 H

[56] References Cited

U.S. PATENT DOCUMENTS

| | | | |
|---|---|---|---|
| 2,776,569 | 1/1957 | Biro | 73/343.5 |
| 3,339,542 | 9/1967 | Howell | 128/2 H |
| 3,623,473 | 11/1971 | Andersen et al. | 73/342 X |
| 3,651,694 | 3/1972 | Lamb | 73/342 |
| 3,699,813 | 10/1972 | Lamb | 73/342 |
| 3,744,555 | 7/1973 | Fletcher et al. | 73/342 X |
| 3,830,224 | 8/1974 | Vanzetti et al. | 128/2 H |
| 3,847,139 | 11/1974 | Flam | 128/2 H |
| 3,880,007 | 4/1975 | Emschermann et al. | 73/362 AR |
| 3,910,257 | 10/1975 | Fletcher et al. | 128/2 H X |
| 3,960,138 | 6/1976 | Doss et al. | 128/2 H |

Primary Examiner—Richard C. Queisser
Assistant Examiner—John S. Appleman
Attorney, Agent, or Firm—Cushman, Darby & Cushman

[57] ABSTRACT

A brassiere which includes a number of skin temperature sensors is described. The sensors are connected to battery operated integrated circuits including storage registers, all, including the battery, integral with the brassiere. The skin temperature at predetermined intervals is recorded and can be "read out" into a printer after long intervals. Hence the brassiere can be worn normally while skin temperature monitoring is carried out at known times. It is believed that these temperature measurements when considered relative to daily and monthly bodily rhythms will be useful in detecting illness, particularly cancer.

14 Claims, 3 Drawing Figures

APPARATUS FOR MAKING SURFACE TEMPERATURE MEASUREMENTS ON THE HUMAN BODY

The present invention relates to apparatus for measuring the surface temperature at points on the human body and particularly, but not exclusively, for measuring surface temperatures at points on the breast.

It is known that areas of a human breast adjacent to a cancerous growth in the breast may be slightly warmer (say 1° or 2° F) than unaffected areas of the other breast. Comparison of the 24-hour temperature variation (circadian variation) between normal and cancerous breasts have shown clear differences in time structure. Such measurements have been made in hospital environments usually with sensors fixed on the skin.

An object of the invention is to provide a special garment which can be worn normally and which allows temperature measurements to be recorded over relatively long periods while the subject lives normally.

According to a first aspect of the present invention there is provided apparatus for measuring surface temperatures at points in the region of the human body, including a garment having a plurality of temperature sensors located therein at spaced apart positions, and means for so storing signals representing output signals from the sensors that the relationship of each signal to time of occurrence can be retrieved.

The time of occurrence may be absolute or relative to the other output signals from the sensors, or to other signals indicative of body functions, for example pulse rate, or to other body rhythms.

Preferably the storage means is mounted on the garment.

The means for storing signals may include means for sampling the output signals of the sensors at predetermined intervals and storage means for storing signals representing the output signals so sampled.

Although the means for storing signals may record continuously, for example on magnetic tape, a sampling technique, using for example tape of a microminiature semiconductor store, is preferable since much less storage capacity is required.

Where it is required to make temperature measurements of the breasts in relation to time the garment may be a brassiere.

Thus, according to a second aspect of the present invention there is provided a brassiere for measuring surface temperatures of the breasts at predetermined points, including a plurality of temperature sensors positioned in each cup of the brassiere, sampling means for sampling the output signals of the sensors at predetermined intervals and storage means for storing the signals so samples, the sampling and storage means being integral with the brassiere.

An advantage of a brassiere according to the invention is that it can be worn normally and allows the rhythm of temperature variations in the breasts to be recorded over relatively long intervals.

The circadian rhythm of breast temperature is regarded as normal feature of the mammary tissue differentiation — a response possibly of a target organ to tides of hormones in the circulation (e.g., 24-h variations in prolactin; menstrual variations in oestrogen). Consequently alterations of the circadian rhythm characteristics occur in breast pathology of which cancer is one example. In this situation the rhythm is sometimes absent and often of altered level and phase. It follows that monitoring breast temperature rhythm over daily and perhaps monthly intervals will be valuable in detection and characterization of disease, e.g., cancer. The present invention stems in part from the realization that variation of temperature with time is important in detecting and characterizing disease so that apparatus according to the invention is able to record a time versus temperature relationship without the disadvantage of making the subject wear anything other than apparently normal garments. No cumbersome additional recorders or trailing wires are necessary.

Preferably the sensors are arranged to form a thermal shield which prevents outward heat flow from the skin at the point where the sensor is located.

After cancer has been detected the garment may be used preoperatively for research into tumours, and if a patient is being treated otherwise than surgically it may be used to assess response to treatment.

Certain embodiments of the invention will now be described, by way of example, with reference to the accompanying drawings, in which.

Figure 1:
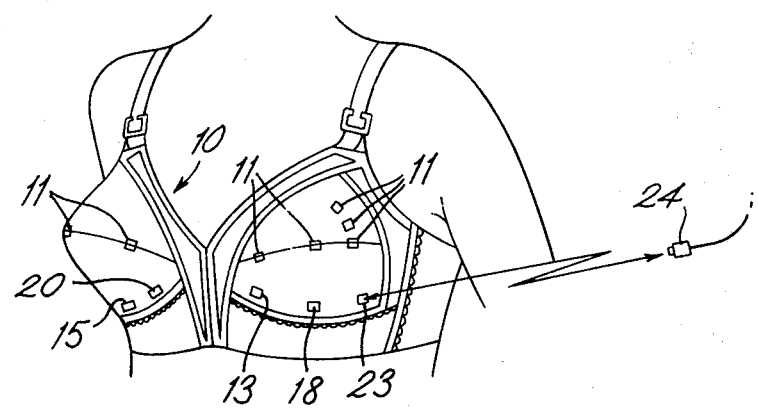
FIG. 1 illustrates a brassiere according to the invention.
Figure 2:
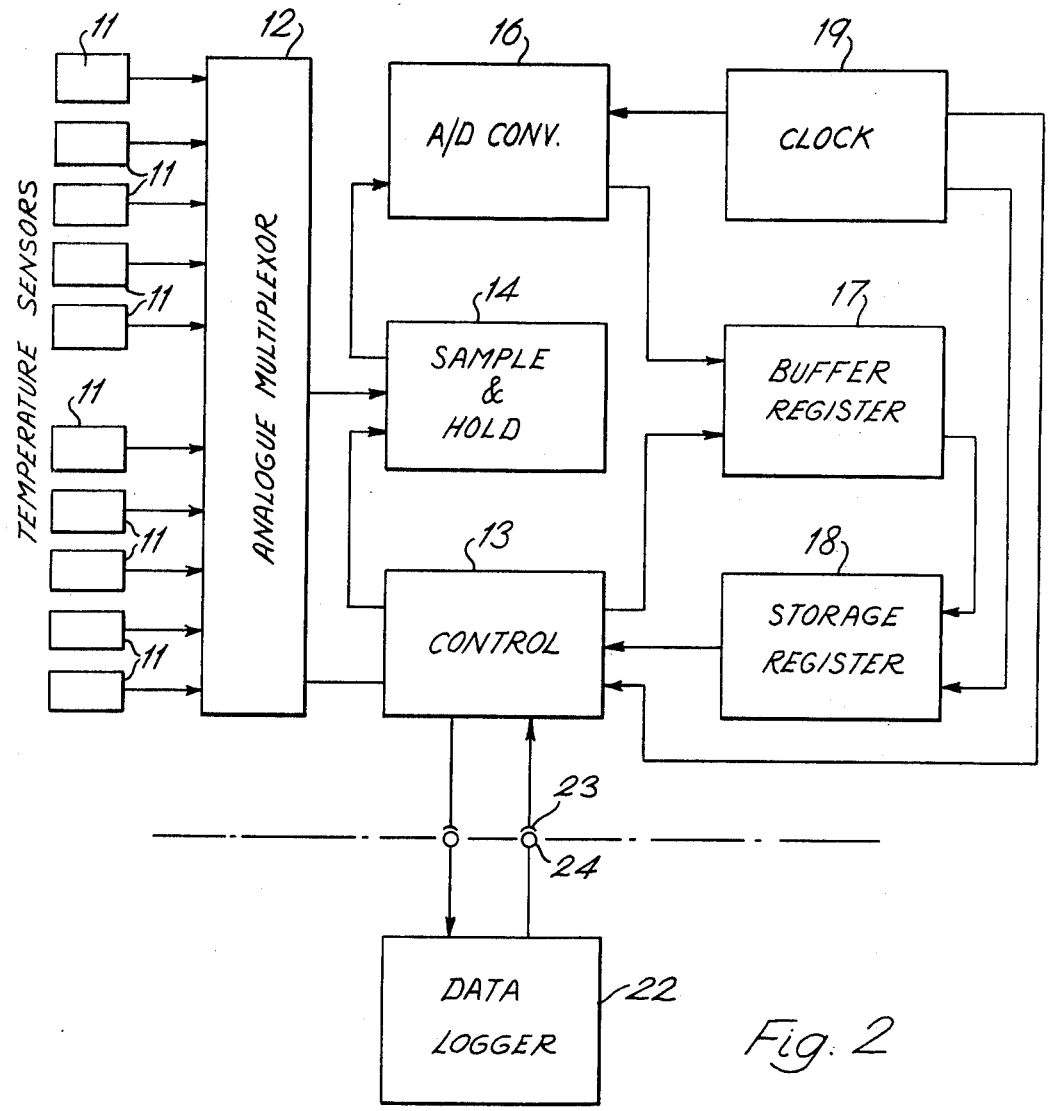
FIG. 2 is a block diagram of the circuit associated with the brassiere of FIG. 1

Referring to FIGS. 1 and 2 a brassiere 10 includes a number of temperature sensors 11 positioned at points where tumors have been shown to occur most frequently.

As shown the sensors are positioned at one, two and three o'clock, over the nipple and at nine o'clock on the left breast, and on the right breast there is a similar concentration of sensors over the upper outward quadrant, that is at nine, ten and eleven o'clock with a sensor over the nipple and one at three o'clock. While these positions are specifically mentioned it will be realised that the sensors may be differently positioned and that different numbers of sensors may be employed.

Each sensor is connected to an analogue multiplexer circuit 12 which on receipt of strobe signals from a control circuit 13 scans the sensors by gating signals one at a time from the sensors to a sample and hold circuit 14. The circuits 12 and 14 of FIG. 2 are contained in a package 15 shown in FIG. 1 but the control circuit 13 is shown in FIGS. 1 and 2.

The signal currently held in the sample and hold circuit 14 is applied to an analogue to digital converter converter 16 and on receipt of a clock pulse from the control circuit 13 the output from the converter 16 is passed to a buffer register 17. Strobe signals from the circuit 13 transfer signals from the buffer register 17 to a storage register 18 of much larger capacity.

An oscillator designated system clock 19 supplies pulses to the control circuit 13 and determines when the sensors are scanned as a group. At, for example, 30 minute intervals, a clock pulse is passed to the control circuit 13 causing each sensor to be scanned within the next 2 or 3 minutes and the circuits are then switched off, except for the system clock, the control circuit and the registers 17 and 18 until the next scanning action takes place in 30 minutes time.

The analogue to digital converter 16, the buffer register 17 and the system clock 19 are in a single package designated 20 in FIG. 1.

After for example 80 hours use the brassiere may be removed and plugged in to data logging apparatus 22 by means of a socket 23 mounted on the brassiere (see FIG. 1) and a plug 24 connected to the data logger 22. Alternatively the data logging apparatus may be connected while temperature readings are being taken, as will be explained. The data logger produces either a tape indicating by means of printed digits the temperatures of the sensors at the various scanning times, or if the data logger includes a digital to analogue converter, a chart recording of the various sensor outputs.

Figure 3:
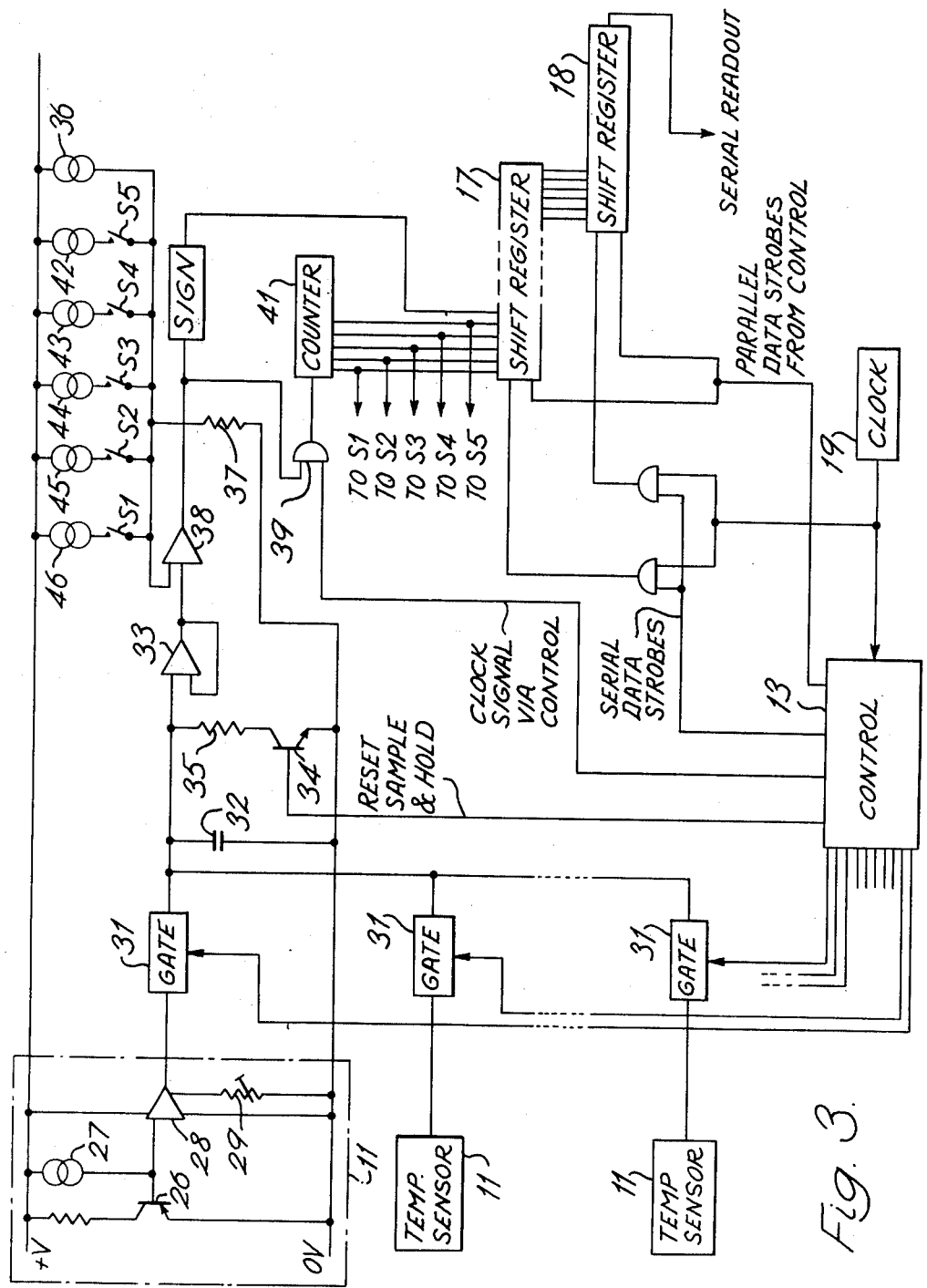
FIG. 3 is a part-circuit diagram of the said circuit.

The various component circuits of FIGS. 1 and 2 will now be discussed in more detail with reference to FIG. 3.

Each sensor may conveniently comprise a silicon transistor 26 mounted on an alumina ceramic base plate (not shown). This plate is fixed in the brassiere so that it presses directly on the skin. The transistor base is supplied from a constant current source 27 and the base emitter voltage is applied to the high impedance input of a buffer amplifier 28 which is adjusted by means of a trimming resistor 29 to provide a predetermined voltage at a fixed temperature of the transistor junction, this fixed temperature being for example 35° C. The temperature coefficient of a silicon junction is stable at about −2.3 millivolts per degree centigrade. The transistor, the constant current source and the amplifier are positioned behind the ceramic plate in the package designated 11 in FIG. 1 and filled with silicon based resin, the complete package having dimensions approximately 10 × 10 × 5 mm. In order to measure a temperature more representative of internal temperatures each sensor may include a heat shield to prevent outward heat flow through the sensor.

The analogue multiplexer circuit 12 comprises a series of MOS transmission gates 31 one associated with each sensor. When open each gate couples its associated sensor to the sample and hold circuit 14. The multiplexer circuit 12 receives strobe pulses from the control circuit 13 which open one gate at a time. Thus the gates in the multiplexer are opened in succession and connect their associated sensors to the sample and hold circuit 14.

A shunt capacitor 32 forms the basis of the sample and hold circuit 14 and is connected to the input of an operational amplifier 33 coupling the capacitor to the analogue to digital converter 16. A transistor 34 in series with a resistor 35 is shunted across the capacitor, and immediately before each gate in the multiplexer 12 is opened a signal is passed to cause the transistor to conduct and discharge the capacitor by way of the resistor.

Any suitable analogue-to-digital converter of the many known types of such converters can be used for the converter 16 but a simple converter will now be briefly described: a constant current source 36 is applied to a shunt resistor 37 and the voltage across the resistor is applied to an operational amplifier 38 forming a comparator. The output from the sample and hold circuit is also applied to the comparator and it will be recalled that each amplifier in the temperature sensors is set to a certain output voltage for a given temperature. The comparator is so set that its output is zero when the sensor supplying the sample and hold circuit is at the given temperature. Usually of course there will be a deviation from this temperature and an output signal will be received from the comparator. This output signal controls the application of pulses by way of a gate 39 to a binary counter 41 which switches in one of five additional weighted constant current sources 42 to 46 as each new count is reached. In this way the voltage from the sample and hold circuit is eventually balanced by switching in a number of weighted constant current sources and the count when balance occurs forms a digital signal which is passed in parallel to the buffer register 17. The initial direction of imbalance at the comparator output provides a sign signal to be passed to the buffer register 17 and also controls in a way not illustrated the sense in which the weighted constant current sources are connected to the input of the comparator.

The signal from the converter 16 consists of five bits plus a sign bit and the buffer register 17 may comprise a 60 bit shift register so that the output from 10 sensors can be held in the shift register. When analogue to digital conversion is complete the control circuit 13 passes a parallel-data strobe pulse to shift register 17 causing parallel readout from the counter 41 to the register 17. Serial-data strobe pulses shift the five bit words along the register and the parallel-data strobe pulses transfers any word reaching the end of the register 17 into the storage register 18 which may conveniently comprise a 10,240 bit shift register. When the data logger 22 is connected the contents of the register 18 are read out in series on application of serial-data strobe pulses to the register from the control circuit 13, but further bits may be stored by the register 17 while read-out is continuing so that temperature monitoring need not be interrupted.

The control circuit 13 includes a counter (not shown) which counts pulses from the clock 19 and at a predetermined count representing an interval of time, say half an hour, switches on the temperature sensors, the analogue multiplexer 12, the analogue to digital converter 16, and the sample and hold circuit 14 which are otherwise disconnected from the battery to conserve current. The various strobe and clock pulses required by the circuit of FIG. 3 are derived by logic circuits which are not described since the design of such circuits for timing the component circuits is well within the competence of designers in the field.

The system clock 19 comprises a stable oscillator providing square wave clock pulses.

A commercially available mains powered desk top printer forms the data logger 22 together with an interface providing a push-button switch to initiate the read-out signal. The digital signals received from the storage register 18 control the printer directly so that as each six bit word is read out the printer converts from binary numbers to decimal and prints out a number indicating the difference between a temperature at which the sensors are set and the measured temperature. At the same time connections (not shown) are made by way of the socket and plug 23 and 24 to charge the battery in the brassiere.

It will be apparent from the foregoing description that the various circuits mounted on the brassiere and the data logger are each in themselves known circuits and in many cases the component circuits are commercially available as complete circuits. Using MOS semiconductor and thick film hybrid microcircuits it is expected that the packages 13, 15, 18, 20 and 23 would each measure approximately 15 × 25 × 5 mm and the battery which consists of a sealed stack of nickel-cadmium cells would be of approximately the same size. The nickel-cadmium cells have a high energy storage capability, inherent safety and long shelf life. Once charged the battery need not be recharged until data are read out and normally such a battery will only need topping up at this stage, and has an indefinite life.

One way of putting the invention into practice has been specifically described but it will, of course, be realized that there are many other ways of implementing the invention. For example the invention can be applied to other garments besides brassieres, the various circuits specifically described can be replaced by a different electronic system and instead of using storage registers other forms of storage such as magnetic recording may be used. Although a sampling rate of once per half hour has been mentioned other rates to suit the temperature rhythm explored, its length and the capacity of storage, may be chosen.

Where some sensors are thought to be more important than others such sensors may be scanned more frequently. Instead of setting each sensor to provide a predetermined output voltage at a predetermined temperature, the temperature from a first sensor may automatically be measured absolutely giving a digital signal with a larger number of bits, and then the signals from the other sensors may be expressed as differences from the measured temperature.

We claim:
1. Apparatus for measuring surface temperatures at points in a region of the human body, including
   a garment,
   a plurality of temperature sensors in the form of semiconductor junctions located in the garment at spaced apart positions,
   means for storing signals representing output signals from the sensors, control means for passing said signals representing output signals from the sensors to said storing means, clock means for producing clock pulses for actuating said control means whereby the time of occurrence relationship of the said output signals stored in said storing means is retained, the storing means, control means, and clock means being integral with the garment.
2. Apparatus according to claim 1 wherein readout means are provided for connecting the storage means to data logging means external to the garment for providing a display representative of the stored signals.
3. Apparatus according to claim 2 wherein the means for storing signals includes
   means for sampling the output signals of the sensors at predetermined intervals, and
   storage means for storing signals representing the output signals so sampled.
4. A brassiere for measuring surface temperatures of the breasts at predetermined points, including
   a plurality of temperature sensors positioned in each cup of the brassiere,
   sampling means for sampling the output signals of the sensors,
   storage means for storing the signals so sampled,
   clock means for producing clock pulses for actuating said storage means whereby the time of occurrence relationship of the said output signals stored in said storage means is retained,
   the sampling means, storage means and clock means being integral with the brassiere.
5. A brassiere according to claim 4 including
   readout means integral with the brassiere for coupling the storage means to data logging means external to the brassiere for providing a display representative of the stored signals.
6. A brassiere according to claim 5 wherein each sensor is arranged to form a thermal shield to prevent heat flow from the skin where the sensor is, in operation, located.
7. A brassiere according to claim 5, incluing
   a multiplexer means integral with the brassiere for coupling each sensor in turn to the storage means when a clock pulse is received by said sampling means.
8. A brassiere according to claim 7 where
   the multiplexer means couples the sensors to the storage means by way of a sample and hold circuits and an analogue to digital converter.
9. A brassiere according to claim 8 wherein the storage means includes
   a first shift register and
   a second shift register of relatively large storage capacity compared with the first shift register,
   the first shift register being coupled to receive digital signals from the analogue to digital converter,
   and the second shift register being coupled to receive digital signals from the first shift register.
10. A brassiere according to claim 5 in combination wih display means, external to the brassiere, for displaying the said stored signals.
11. A brassiere according to claim 10 wherein the display means displays the stored signals by printing.
12. A brassiere according to claim 4 wherein said storage means, sampling means and clock means are positioned in a plurality of packages spaced apart from one another, and integral with the brassiere.
13. A brassiere according to claim 12 including a rechargeable battery mounted on the brassiere.
14. A brassiere according to claim 4 wherein each sensor comprises a semiconductor junction.

* * * * *